United States Patent [19]

Nainan et al.

[11] Patent Number: 5,430,135
[45] Date of Patent: Jul. 4, 1995

[54] DNA SEQUENCE ENCODING A CYNOMOLGUS MONKEY HEPATITIS A VIRUS CAPSID PROTEIN

[75] Inventors: Omana V. Nainan, Decatur; Harold S. Margolis, Lilburn; Betty H. Robertson, Chamblee; Margo A. Brinton, Atlanta; James W. Ebert, Lilburn, all of Ga.

[73] Assignee: The United States of America as represented by the Department of Health and Human Services, Washington, D.C.

[21] Appl. No.: 87,016

[22] Filed: Jul. 6, 1993

Related U.S. Application Data

[63] Continuation of Ser. No. 678,828, Apr. 3, 1991, abandoned.

[51] Int. Cl.6 .................. C07H 17/00; C12P 21/02; C12P 19/34; C12N 15/00
[52] U.S. Cl. .................. 536/23.72; 435/69.1; 435/172.3; 435/235.1; 435/240.2; 530/350; 935/9; 935/32; 935/34; 935/57; 935/63; 935/70

[58] Field of Search .................. 435/235.1, 69.1, 91, 435/172.3; 424/240.2, 89; 536/27.1, 23.72; 530/350; 935/9, 32, 34, 57, 63, 70

[56] References Cited

PUBLICATIONS

Reeck et al Cell vol. 50 p. 667 (1987).
Lewin Science vol. 237–Sep. 25, 1987.
Barardy eta l Proc Natl Acad Sci USA vol. 82 pp. 2143–2147 (1985).
Lemon et al J. Virol vol. 61 pp. 735–742 (1987).
Balayan et al. FEBS Lett vol. 247 pp. 425–428 (1989).
Brown et al.

*Primary Examiner*—Joan Ellis
*Attorney, Agent, or Firm*—Townsend and Townsend Khourie and Crew

[57] ABSTRACT

The present invention relates, in general, to substantially pure preparations of the cynomolgus monkey hepatitis A viral isolates CY-145 and CY-55/JM-55; cDNAs of the genomic RNAs of cynomolgus monkey hepatitis A viral isolates CY-145 and CY-55/JM-55; a method of preventing hepatitis A in an animal; and vaccines comprising the cynomolgus monkey hepatitis A viral isolates CY-145 and CY-55/JM-55.

3 Claims, 12 Drawing Sheets

```
                    →VPO
  1    ATGAATGAAATATGGCTAGACAAGGATTGTTTCAGACTGTTGGTAGTGGCCTTGACCACATT
        M  N  M  A  R  Q  G  L  F  Q  T  V  G  S  G  L  D  H  I

61    CTTTCTTTGGCTGACGTCGAGGAAGAGCAAATGATTCAATCTGTTGATAGAACAGCTGTG
        L  S  L  A  D  V  E  E  E  Q  M  I  Q  S  V  D  R  T  A  V

121    ACTGGAGCTTCATACTTCACTTCTGTAGACCAATCTTCAGTTCCATACAGCAGAAGTTGGT
        T  G  A  S  Y  F  T  S  V  D  Q  S  S  V  H  T  A  E  V  G

181    TCTCATCAATCAGAGCCTTTGAAAACCTCAGTTGATAAACCAGGCTCAAAAAGACACAG
        S  H  Q  S  E  P  L  K  T  S  V  D  K  P  G  S  K  K  T  Q

241    GGTGAGAAATTTTTCCTCATTCATTCAGCTGATTGGTTGTCTACGCATGCTTTATTTCAT
        G  E  K  F  F  L  I  H  S  A  D  W  L  S  T  H  A  L  F  H

301    GAGGTGGCCAAGCTTGATGTGGTTAGTTTGCTTTATAATGAGCAATTGCAGTCCAAGGA
        E  V  A  K  L  D  V  V  S  L  L  Y  N  E  Q  F  A  V  Q  G

361    TTGTTGAGATATCACACTTATGCTAGGTTTGGAATTGAGATTCAAGTTCAAATAAATCCT
        L  L  R  Y  H  T  Y  A  R  F  G  I  E  I  Q  V  Q  I  N  P

421    ACTCCTTTTCAACAAGGAGGACTAATTTGTGCTATGGTTCCTGGGGATCAAGGCTATGGG
        T  P  F  Q  Q  G  G  L  I  C  A  M  V  P  G  D  Q  G  Y  G

FIG. 3-1.
```

```
481  ............AT.A.....C.....T..C.....A
     TCTATTGCTTCTCTCACTGTTTATCCACATGGTTTGCTGAATTGTAATATCAATAATGTG
      S   I   A   S   L   T   V   Y   P   H   G   L   L   N   C   N   I   N   N   V

541  ..A........GT.C..T..C............T.......T..A..T..A..G
     GTTAGAATCAAAGTTCCATTTATTTATACTAGAGGAGCTTACCATTTCAAGGACCCCCAA
      V   R   I   K   V   P   F   I   Y   T   R   G   A   Y   H   F   K   D   P   Q
                      F

601  ..T..A..C.....C.T......TC.T..G......T..GC............T...
     TACCCTGTTTGGGAATTAACAATCAGAGTATGGTCAGAATTCAATATTGGAACTGGAACT
      Y   P   V   W   E   L   T   I   R   V   W   S   E   F   N   I   G   T   G   T
                                                      L

661  .............A..T.G............GC.T..........CT.G
     TCTGCATACACGTCATTGAATGTATTAGCTAGATTTACTGATCTTGAGTTGCATGGTCTC
      S   A   Y   T   S   L   N   V   L   A   R   F   T   D   L   E   L   H   G   L

721  .............T....➝VP3............A..T.....A..T...G.....A
     ACTCCATTGTCTACCCAGATGATGAGAAATGAATTTAGGGTGAGTACCACAGAAAATGTT
      T   P   L   S   T   Q   M   M   R   N   E   F   R   V   S   T   T   E   N   V
```

FIG. 3-2.

```
781  ....T.G..C.......G..T.T........TC.....................A
     GTTAATCTTTCTAATTATGAAGACGCAAGAGCAAAAATGTCATTTGCATTGGATCAAGAG
     V  N  L  S  N  Y  E  D  A  R  A  K  M  S  F  A  L  D  Q  E

841  G.......A........CC...A..T...G.T..A..C.......A.A..A....
     AATTGGAGATCTGATCCATCTGAGGGTGGAGGAATCAAGATTACTCATTTCTCTACTTGG
     N  W  R  S  D  P  S  E  G  G  G  I  K  I  T  H  F  S  T  W
     D     K           Q           V

901  ......T.C......T.............A........T........A
     ACCTCAATACCAACTTTGGCAGCTCAGTTTGCTTTTAATGCTTCAGTTGGGACAG
     T  S  I  P  T  L  A  A  Q  F  A  F  N  A  S  V  G  Q
                                               *

961  ..A..............T.................
     CAGATTAAGGTTATACCTGTTGATCCATATTTTTATCAAATGACAAATTCAAATCCTGAT
     Q  I  K  V  I  P  V  D  P  Y  F  Y  Q  M  T  N  S  N  P  D

1021 CAGAAAATACATTACTGCTTTAGCTTTCAATTGTCAGATGTTTTGTTTTTGGAGAGGAGAT
     Q  K  Y  I  T  A  L  A  S  I  C  Q  M  F  C  F  W  R  G  D
```

FIG. 3-3.

```
1081  TTAGTTTTTGATTTTCAAGTTTTTCCTACAAAGTATCATTCAGGAAGATTGCAATTTTGT
       L  V  F  D  F  Q  V  F  P  T  K  Y  H  S  G  R  L  Q  F  C

1141  TTTGTACCTGGAAATGAGTTAATTGAAGTAACTTCTATAACATTGAAACAGGCTACTACT
       F  V  P  G  N  E  L  I  E  V  T  S  I  T  L  K  Q  A  T  T

1201  GCCCCATGTGCAGTGATGGACATTACAGGAGTACAATGACACTAAGATTTCGAGTCCCT
       A  P  C  A  V  M  D  I  T  G  V  Q  S  T  L  R  F  R  V  P

1261  TGGATCTCAGATACTCCTTACAGAGTCAATTGTTATATTAAGTCCTCACATCAGAAGGT
       W  I  S  D  T  P  Y  R  V  N  C  Y  I  K  S  S  H  Q  K  G

1321  GAATATACAGGCGATTGAAAAATTGATTGTTTACTGTTACAACAGATTGACTTCTCCTTCT
       E  Y  T  A  I  E  K  L  I  V  Y  C  Y  N  R  L  T  S  P  S

1381  AATGTTGCATCCCATGTCAGAGTTAACGTTTATCTGTCAGCAATCAATTGGAGTGCTTT
       N  V  A  S  H  V  R  V  N  V  Y  L  S  A  I  N  L  E  C  F
```

FIG. 3-4.

```
                        T.....C..G┌.G....T....T...T...
       GCTCCACTATATCATGCTATGGATGTCACATCTCAAACTGGAGATGACTCAGGAGGCTTT
                                  └→VPI
1441    A  P  L  Y  H  A  M  D  V  T  S  Q  T  G  D  D  S  G  G  F

..A......T.....A...G....CT........T.G....T.......AATC.
       TCTACTACTGTGTTTCCACTGAGCAAAATGTGCCTGATCCGCAAGTTGGAATTACAACTCCA
1501    S  T  T  V  S  T  E  Q  N  V  P  D  P  Q  V  G  I  T  T  P
                                    A                              I

....T.....A.....A.....GA....A..........C..C....T..A
       AAGGACTTGAAGGGAAAGGCTAATAAGGGAAAGATGATGTTTCTGGTGTTCAAGCCCCT
1561    K  D  L  K  G  K  A  N  K  G  K  M  D  V  S  G  V  Q  A  P

....T..T.C....T.....A..........GT.A..C....AA.......A..A..T
       GTTGGAGCAATAACAACAATAGAGGATCCAGTTCTTGCTAAGAAGGTTCCTGAGACCTTC
1621    V  G  A  I  T  I  E  D  P  V  L  A  K  K  V  P  E  T  F
                                          I

..A..G......A.....G......A................A.T........
       CCTGAATTGAAGCCTGGTGAATCTAGGCATACATCTGATCACATGTCTGTGTACAAATTT
1681    P  E  L  K  P  G  E  S  R  H  T  S  D  H  M  S  V  Y  K  F
                                                I
```

*FIG. 3-5.*

```
1741  .........C..T......C..T.................C..T..A..........C
      ATGGGAAGGTCACATTTCTTGTGCACTTTTACATTTAATGCAAATAACAGGGAATATACT
       M  G  R  S  H  F  L  C  T  F  F  N  A  N  N  R  E  Y  T

1801  ...........T..G..T......A..T.........C......T.TG.....A..T..AC..
      TTCCAATAACCTTATCATCAACTTCAAATCCTCCACATGGATCTCCACATTGAGG
       F  P  I  T  L  S  S  T  S  N  P  P  H  G  S  P  S  T  L  R
                                                    *

1861  ........C.....T..G..............G..........A..AC.G............T..T.......A
      TGGTTTTTAACCTTATTTCAGCTCTATAGAGGCCCGTTAGATTGACTATCATCATCACT
       W  F  F  N  L  F  Q  L  Y  R  G  P  L  D  L  T  I  I  T

1921  ...........T.............G................C......G.....C..T...C..T..C...T
      GGAGCCACAGATGTTGATGGAATGGCATGGTTCACACCTGTTGGTTTGGCTGTAGATACC
       G  A  T  D  V  D  G  M  A  W  F  T  P  V  G  L  A  V  D  T

1981  ........G..A...............G..A........A...T.A..T..........G..A...........G.....T
      CCTTGGGTAGAGAAGCAGTCTCTGCTCTGACAATTGATTATAAAACTGCTTTGGGAGCTATC
       P  W  V  E  K  Q  S  A  L  T  I  D  Y  K  T  A  L  G  A  I
```

FIG. 3-6.

```
2041  ......T..C..........C..................C.T..G.....T...........
      AGATTAACACGAGAAGAACTGGGAACATTCAAATTAGATTGCCTTGGTACTCATATCTT
       R  F  N  T  R  R  T  G  N  I  Q  I  R  L  P  W  Y  S  Y  L

2101  .....T....T..C...A
      TATGCAGTGTCAGTGCTCTGGATGGACTTGGAGATACAACGGACTCAACTTTTGGTCTA
       Y  A  V  S  G  A  L  D  G  L  G  D  T  T  D  S  T  F  G  L

2161  GTTTCTATACAGATTGCAAATTACAATCACTCTGATGAATACTTGTCTTTTAGTTGTTAT
       V  S  I  Q  I  A  N  Y  N  H  S  D  E  Y  L  S  F  S  C  Y

2221  TTGTCTGTGTTACAGAACAATTCTGAATTTTTCTTTTTCCTAGGGCTCCTTTGAATTCAAGTGCT
       L  S  V  T  E  Q  S  E  F  F  F  F  P  R  A  P  L  N  S  S  A

2281  ATGATGACTTCTGAAAATATGTTAGACAGAATTGCTGGAGGTGATCTTGAGTCGTCAGTA
       M  M  T  S  E  N  M  L  D  R  I  A  G  G  D  L  E  S  S  V

┌─── P2
2341  GATGACCCCCGTACAGATGAAGATCGTAGATTTGAGAGTCATATTGAGAAGAAACCATAC
       D  D  P  R  T  D  E  D  R  R  F  E  S  H  I  E  K  K  P  Y
```

FIG. 3-7.

2401 AAGGAGTTGAGACTTGAGGTTGGTAAGCAGAGATTCAAATATGCAAGAGAAGAGAATTGTCA
     K  E  L  R  L  E  V  G  K  Q  R  F  K  Y  A  R  E  E  L  S

2461 AATGAGATCTTGCCTCCCCCCTAGGAAATTGAAAGGATTGTTTTCACAATCAAAAATTTCC
     N  E  I  L  P  P  P  P  R  K  L  K  G  L  F  S  Q  S  K  I  S

FIG. 3-8.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2520 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 4..2520

( x i ) SEQUENCE DESCRIPTION: SEQ ID NO:1:

```
ATG ATG AAT ATG GCT AGA CAA GGA TTG TTT CAG ACT GTT GGT AGT GGC       48
    Met Asn Met Ala Arg Gln Gly Leu Phe Gln Thr Val Gly Ser Gly
    1               5                   10                  15

CTT GAC CAC ATT CTT TCT TTG GCT GAC GTC GAG GAA GAG CAA ATG ATT       96
Leu Asp His Ile Leu Ser Leu Ala Asp Val Glu Glu Glu Gln Met Ile
                20                  25                  30

CAA TCT GTT GAT AGA ACA GCT GTG ACT GGA GCT TCA TAC TTC ACT TCT      144
Gln Ser Val Asp Arg Thr Ala Val Thr Gly Ala Ser Tyr Phe Thr Ser
            35                  40                  45

GTA GAC CAA TCT TCA GTC CAT ACA GCA GAA GTT GGT TCT CAT CAA TCA      192
Val Asp Gln Ser Ser Val His Thr Ala Glu Val Gly Ser His Gln Ser
        50                  55                  60

GAG CCT TTG AAA ACC TCA GTT GAT AAA CCA GGC TCA AAA AAG ACA CAG      240
Glu Pro Leu Lys Thr Ser Val Asp Lys Pro Gly Ser Lys Lys Thr Gln
    65                  70                  75

GGT GAG AAA TTT TTC CTC ATT CAT TCA GCT GAT TGG TTG TCT ACG CAT      288
Gly Glu Lys Phe Phe Leu Ile His Ser Ala Asp Trp Leu Ser Thr His
80                  85                  90                  95

GCT TTA TTT CAT GAG GTG GCC AAG CTT GAT GTG GTT AGT TTG CTT TAT      336
Ala Leu Phe His Glu Val Ala Lys Leu Asp Val Val Ser Leu Leu Tyr
                100                 105                 110

AAT GAG CAA TTT GCA GTC CAA GGA TTG TTG AGA TAT CAC ACT TAT GCT      384
Asn Glu Gln Phe Ala Val Gln Gly Leu Leu Arg Tyr His Thr Tyr Ala
            115                 120                 125

AGG TTT GGA ATT GAG ATT CAA GTT CAA ATA AAT CCT ACT CCT TTT CAA      432
Arg Phe Gly Ile Glu Ile Gln Val Gln Ile Asn Pro Thr Pro Phe Gln
        130                 135                 140

CAA GGA GGA CTA ATT TGT GCT ATG GTT CCT GGG GAT CAA GGC TAT GGG      480
Gln Gly Gly Leu Ile Cys Ala Met Val Pro Gly Asp Gln Gly Tyr Gly
    145                 150                 155
```

| | | | | | | | | | | | | | | | | |
|---|---|---|---|---|---|---|---|---|---|---|---|---|---|---|---|---|
| TCT | ATT | GCT | TCT | CTC | ACT | GTT | TAT | CCA | CAT | GGT | TTG | CTG | AAT | TGT | AAT | 528 |
| Ser | Ile | Ala | Ser | Leu | Thr | Val | Tyr | Pro | His | Gly | Leu | Leu | Asn | Cys | Asn | |
| 160 | | | | | 165 | | | | 170 | | | | | | 175 | |
| ATC | AAT | AAT | GTG | GTT | AGA | ATC | AAA | GTT | CCA | TTT | ATT | TAT | ACT | AGA | GGA | 576 |
| Ile | Asn | Asn | Val | Val | Arg | Ile | Lys | Val | Pro | Phe | Ile | Tyr | Thr | Arg | Gly | |
| | | | | 180 | | | | | 185 | | | | | 190 | | |
| GCT | TAC | CAT | TTC | AAG | GAC | CCC | CAA | TAC | CCT | GTT | TGG | GAA | TTA | ACA | ATC | 624 |
| Ala | Tyr | His | Phe | Lys | Asp | Pro | Gln | Tyr | Pro | Val | Trp | Glu | Leu | Thr | Ile | |
| | | | 195 | | | | 200 | | | | | 205 | | | | |
| AGA | GTA | TGG | TCA | GAA | TTC | AAT | ATT | GGA | ACT | GGA | ACT | TCT | GCA | TAC | ACG | 672 |
| Arg | Val | Trp | Ser | Glu | Phe | Asn | Ile | Gly | Thr | Gly | Thr | Ser | Ala | Tyr | Thr | |
| | | 210 | | | | | 215 | | | | | 220 | | | | |
| TCA | TTG | AAT | GTA | TTA | GCT | AGA | TTT | ACT | GAT | CTT | GAG | TTG | CAT | GGT | CTC | 720 |
| Ser | Leu | Asn | Val | Leu | Ala | Arg | Phe | Thr | Asp | Leu | Glu | Leu | His | Gly | Leu | |
| 225 | | | | | 230 | | | | | 235 | | | | | | |
| ACT | CCA | TTG | TCT | ACC | CAG | ATG | ATG | AGA | AAT | GAA | TTT | AGG | GTG | AGT | ACC | 768 |
| Thr | Pro | Leu | Ser | Thr | Gln | Met | Met | Arg | Asn | Glu | Phe | Arg | Val | Ser | Thr | |
| 240 | | | | | 245 | | | | | 250 | | | | | 255 | |
| ACA | GAA | AAT | GTT | GTT | AAT | CTT | TCT | AAT | TAT | GAA | GAC | GCA | AGA | GCA | AAA | 816 |
| Thr | Glu | Asn | Val | Val | Asn | Leu | Ser | Asn | Tyr | Glu | Asp | Ala | Arg | Ala | Lys | |
| | | | | 260 | | | | | 265 | | | | | 270 | | |
| ATG | TCA | TTT | GCA | TTG | GAT | CAA | GAG | AAT | TGG | AGA | TCT | GAT | CCA | TCT | GAG | 864 |
| Met | Ser | Phe | Ala | Leu | Asp | Gln | Glu | Asn | Trp | Arg | Ser | Asp | Pro | Ser | Glu | |
| | | | 275 | | | | | 280 | | | | | 285 | | | |
| GGT | GGA | GGA | ATC | AAG | ATT | ACT | CAT | TTC | TCT | ACT | TGG | ACC | TCA | ATA | CCA | 912 |
| Gly | Gly | Gly | Ile | Lys | Ile | Thr | His | Phe | Ser | Thr | Trp | Thr | Ser | Ile | Pro | |
| | | 290 | | | | | 295 | | | | | 300 | | | | |
| ACT | TTG | GCA | GCT | CAG | TTT | GCT | TTT | AAT | GCT | TCA | GCT | TCA | GTG | GGA | CAG | 960 |
| Thr | Leu | Ala | Ala | Gln | Phe | Ala | Phe | Asn | Ala | Ser | Ala | Ser | Val | Gly | Gln | |
| 305 | | | | | 310 | | | | | 315 | | | | | | |
| CAG | ATT | AAG | GTT | ATA | CCT | GTT | GAT | CCA | TAT | TTT | TAT | CAA | ATG | ACA | AAT | 1008 |
| Gln | Ile | Lys | Val | Ile | Pro | Val | Asp | Pro | Tyr | Phe | Tyr | Gln | Met | Thr | Asn | |
| 320 | | | | | 325 | | | | | 330 | | | | | 335 | |
| TCA | AAT | CCT | GAT | CAG | AAA | TAC | ATT | ACT | GCT | TTA | GCT | TCA | ATT | TGT | CAG | 1056 |
| Ser | Asn | Pro | Asp | Gln | Lys | Tyr | Ile | Thr | Ala | Leu | Ala | Ser | Ile | Cys | Gln | |
| | | | | 340 | | | | | 345 | | | | | 350 | | |
| ATG | TTT | TGT | TTT | TGG | AGA | GGA | GAT | TTA | GTT | TTT | GAT | TTT | CAA | GTT | TTT | 1104 |
| Met | Phe | Cys | Phe | Trp | Arg | Gly | Asp | Leu | Val | Phe | Asp | Phe | Gln | Val | Phe | |
| | | | 355 | | | | | 360 | | | | | 365 | | | |
| CCT | ACA | AAG | TAT | CAT | TCA | GGA | AGA | TTG | CAA | TTT | TGT | TTT | GTA | CCT | GGA | 1152 |
| Pro | Thr | Lys | Tyr | His | Ser | Gly | Arg | Leu | Gln | Phe | Cys | Phe | Val | Pro | Gly | |
| | | 370 | | | | | 375 | | | | | 380 | | | | |
| AAT | GAG | TTA | ATT | GAA | GTA | ACT | TCT | ATA | ACA | TTG | AAA | CAG | GCT | ACT | ACT | 1200 |
| Asn | Glu | Leu | Ile | Glu | Val | Thr | Ser | Ile | Thr | Leu | Lys | Gln | Ala | Thr | Thr | |
| | | 385 | | | | | 390 | | | | | 395 | | | | |
| GCC | CCA | TGT | GCA | GTG | ATG | GAC | ATT | ACA | GGA | GTA | CAA | TCG | ACA | CTA | AGA | 1248 |
| Ala | Pro | Cys | Ala | Val | Met | Asp | Ile | Thr | Gly | Val | Gln | Ser | Thr | Leu | Arg | |
| 400 | | | | | 405 | | | | | 410 | | | | | 415 | |
| TTT | CGA | GTC | CCT | TGG | ATC | TCA | GAT | ACT | CCT | TAC | AGA | GTC | AAT | TGT | TAT | 1296 |
| Phe | Arg | Val | Pro | Trp | Ile | Ser | Asp | Thr | Pro | Tyr | Arg | Val | Asn | Cys | Tyr | |
| | | | | 420 | | | | | 425 | | | | | 430 | | |
| ATT | AAG | TCC | TCA | CAT | CAG | AAG | GGT | GAA | TAT | ACA | GCG | ATT | GAA | AAA | TTG | 1344 |
| Ile | Lys | Ser | Ser | His | Gln | Lys | Gly | Glu | Tyr | Thr | Ala | Ile | Glu | Lys | Leu | |
| | | | 435 | | | | | 440 | | | | | 445 | | | |
| ATT | GTT | TAC | TGT | TAC | AAC | AGA | TTG | ACT | TCT | CCT | TCT | AAT | GTT | GCA | TCC | 1392 |
| Ile | Val | Tyr | Cys | Tyr | Asn | Arg | Leu | Thr | Ser | Pro | Ser | Asn | Val | Ala | Ser | |
| | | 450 | | | | | 455 | | | | | 460 | | | | |
| CAT | GTC | AGA | GTT | AAC | GTT | TAT | CTG | TCA | GCA | ATC | AAT | TTG | GAG | TGC | TTT | 1440 |
| His | Val | Arg | Val | Asn | Val | Tyr | Leu | Ser | Ala | Ile | Asn | Leu | Glu | Cys | Phe | |
| | | 465 | | | | | 470 | | | | | 475 | | | | |
| GCT | CCA | CTA | TAT | CAT | GCT | ATG | GAT | GTC | ACA | TCT | CAA | ACT | GGA | GAT | GAC | 1488 |

|   |   |   |   |   |   |   |   |   |   |   |   |   |   |   |   |
|---|---|---|---|---|---|---|---|---|---|---|---|---|---|---|---|
| Ala | Pro | Leu | Tyr | His | Ala | Met | Asp | Val | Thr | Ser | Gln | Thr | Gly | Asp | Asp |
| 480 |   |   |   |   | 485 |   |   |   | 490 |   |   |   |   |   | 495 |

| TCA | GGA | GGC | TTT | TCT | ACT | ACT | GTT | TCC | ACT | GAG | CAA | AAT | GTG | CCT | GAT | 1536 |
|---|---|---|---|---|---|---|---|---|---|---|---|---|---|---|---|---|
| Ser | Gly | Gly | Phe | Ser | Thr | Thr | Val | Ser | Thr | Glu | Gln | Asn | Val | Pro | Asp |  |
|   |   |   |   | 500 |   |   |   |   | 505 |   |   |   |   | 510 |   |  |

| CCG | CAA | GTT | GGA | ATT | ACA | ACT | CCA | AAG | GAC | TTG | AAG | GGG | AAG | GCT | AAT | 1584 |
|---|---|---|---|---|---|---|---|---|---|---|---|---|---|---|---|---|
| Pro | Gln | Val | Gly | Ile | Thr | Thr | Pro | Lys | Asp | Leu | Lys | Gly | Lys | Ala | Asn |  |
|   |   |   |   | 515 |   |   |   |   | 520 |   |   |   |   | 525 |   |  |

| AAG | GGA | AAG | ATG | GAT | GTT | TCT | GGT | GTT | CAA | GCC | CCT | GTT | GGA | GCA | ATA | 1632 |
|---|---|---|---|---|---|---|---|---|---|---|---|---|---|---|---|---|
| Lys | Gly | Lys | Met | Asp | Val | Ser | Gly | Val | Gln | Ala | Pro | Val | Gly | Ala | Ile |  |
|   |   |   | 530 |   |   |   |   | 535 |   |   |   |   | 540 |   |   |  |

| ACA | ACA | ATA | GAG | GAT | CCA | GTT | CTT | GCT | AAG | AAG | GTT | CCT | GAG | ACC | TTC | 1680 |
|---|---|---|---|---|---|---|---|---|---|---|---|---|---|---|---|---|
| Thr | Thr | Ile | Glu | Asp | Pro | Val | Leu | Ala | Lys | Lys | Val | Pro | Glu | Thr | Phe |  |
|   |   | 545 |   |   |   |   | 550 |   |   |   |   | 555 |   |   |   |  |

| CCT | GAA | TTG | AAG | CCT | GGT | GAA | TCT | AGG | CAT | ACA | TCT | GAT | CAC | ATG | TCT | 1728 |
|---|---|---|---|---|---|---|---|---|---|---|---|---|---|---|---|---|
| Pro | Glu | Leu | Lys | Pro | Gly | Glu | Ser | Arg | His | Thr | Ser | Asp | His | Met | Ser |  |
| 560 |   |   |   |   | 565 |   |   |   |   | 570 |   |   |   |   | 575 |  |

| GTG | TAC | AAA | TTT | ATG | GGA | AGG | TCA | CAT | TTC | TTG | TGC | ACT | TTT | ACA | TTT | 1776 |
|---|---|---|---|---|---|---|---|---|---|---|---|---|---|---|---|---|
| Val | Tyr | Lys | Phe | Met | Gly | Arg | Ser | His | Phe | Leu | Cys | Thr | Phe | Thr | Phe |  |
|   |   |   |   | 580 |   |   |   |   | 585 |   |   |   |   | 590 |   |  |

| AAT | GCA | AAT | AAC | AGG | GAA | TAT | ACT | TTT | CCA | ATA | ACC | TTA | TCA | TCA | ACT | 1824 |
|---|---|---|---|---|---|---|---|---|---|---|---|---|---|---|---|---|
| Asn | Ala | Asn | Asn | Arg | Glu | Tyr | Thr | Phe | Pro | Ile | Thr | Leu | Ser | Ser | Thr |  |
|   |   |   |   | 595 |   |   |   |   | 600 |   |   |   |   | 605 |   |  |

| TCA | AAT | CCT | CCA | CAT | GGA | TCT | CCA | TCC | ACA | TTG | AGG | TGG | TTT | TTT | AAC | 1872 |
|---|---|---|---|---|---|---|---|---|---|---|---|---|---|---|---|---|
| Ser | Asn | Pro | Pro | His | Gly | Ser | Pro | Ser | Thr | Leu | Arg | Trp | Phe | Phe | Asn |  |
|   |   | 610 |   |   |   |   | 615 |   |   |   |   | 620 |   |   |   |  |

| CTA | TTT | CAG | CTC | TAT | AGA | GGC | CCG | TTA | GAT | TTG | ACT | ATC | ATC | ATC | ACT | 1920 |
|---|---|---|---|---|---|---|---|---|---|---|---|---|---|---|---|---|
| Leu | Phe | Gln | Leu | Tyr | Arg | Gly | Pro | Leu | Asp | Leu | Thr | Ile | Ile | Ile | Thr |  |
|   | 625 |   |   |   |   | 630 |   |   |   |   | 635 |   |   |   |   |  |

| GGA | GCC | ACA | GAT | GTT | GAT | GGA | ATG | GCA | TGG | TTC | ACA | CCT | GTT | GGT | TTG | 1968 |
|---|---|---|---|---|---|---|---|---|---|---|---|---|---|---|---|---|
| Gly | Ala | Thr | Asp | Val | Asp | Gly | Met | Ala | Trp | Phe | Thr | Pro | Val | Gly | Leu |  |
| 640 |   |   |   |   | 645 |   |   |   |   | 650 |   |   |   |   | 655 |  |

| GCT | GTA | GAT | ACC | CCT | TGG | GTA | GAG | AAG | CAG | TCT | GCT | CTG | ACA | ATT | GAT | 2016 |
|---|---|---|---|---|---|---|---|---|---|---|---|---|---|---|---|---|
| Ala | Val | Asp | Thr | Pro | Trp | Val | Glu | Lys | Gln | Ser | Ala | Leu | Thr | Ile | Asp |  |
|   |   |   |   | 660 |   |   |   |   | 665 |   |   |   |   | 670 |   |  |

| TAT | AAA | ACT | GCT | TTG | GGA | GCT | ATC | AGA | TTT | AAC | ACG | AGA | AGA | ACT | GGG | 2064 |
|---|---|---|---|---|---|---|---|---|---|---|---|---|---|---|---|---|
| Tyr | Lys | Thr | Ala | Leu | Gly | Ala | Ile | Arg | Phe | Asn | Thr | Arg | Arg | Thr | Gly |  |
|   |   |   | 675 |   |   |   |   | 680 |   |   |   |   | 685 |   |   |  |

| AAC | ATT | CAA | ATT | AGA | TTG | CCT | TGG | TAC | TCA | TAT | CTT | TAT | GCA | GTG | TCA | 2112 |
|---|---|---|---|---|---|---|---|---|---|---|---|---|---|---|---|---|
| Asn | Ile | Gln | Ile | Arg | Leu | Pro | Trp | Tyr | Ser | Tyr | Leu | Tyr | Ala | Val | Ser |  |
|   |   | 690 |   |   |   |   | 695 |   |   |   |   | 700 |   |   |   |  |

| GGT | GCT | CTG | GAT | GGA | CTT | GGA | GAT | ACA | ACG | GAC | TCA | ACT | TTT | GGT | CTA | 2160 |
|---|---|---|---|---|---|---|---|---|---|---|---|---|---|---|---|---|
| Gly | Ala | Leu | Asp | Gly | Leu | Gly | Asp | Thr | Thr | Asp | Ser | Thr | Phe | Gly | Leu |  |
| 705 |   |   |   |   | 710 |   |   |   |   | 715 |   |   |   |   |   |  |

| GTT | TCT | ATA | CAG | ATT | GCA | AAT | TAC | AAT | CAC | TCT | GAT | GAA | TAC | TTG | TCT | 2208 |
|---|---|---|---|---|---|---|---|---|---|---|---|---|---|---|---|---|
| Val | Ser | Ile | Gln | Ile | Ala | Asn | Tyr | Asn | His | Ser | Asp | Glu | Tyr | Leu | Ser |  |
| 720 |   |   |   |   | 725 |   |   |   |   | 730 |   |   |   |   | 735 |  |

| TTT | AGT | TGT | TAT | TTG | TCT | GTT | ACA | GAA | CAA | TCT | GAA | TTT | TTC | TTT | CCT | 2256 |
|---|---|---|---|---|---|---|---|---|---|---|---|---|---|---|---|---|
| Phe | Ser | Cys | Tyr | Leu | Ser | Val | Thr | Glu | Gln | Ser | Glu | Phe | Phe | Phe | Pro |  |
|   |   |   |   | 740 |   |   |   |   | 745 |   |   |   |   | 750 |   |  |

| AGG | GCT | CCT | TTG | AAT | TCA | AGT | GCT | ATG | ATG | ACT | TCT | GAA | AAT | ATG | TTA | 2304 |
|---|---|---|---|---|---|---|---|---|---|---|---|---|---|---|---|---|
| Arg | Ala | Pro | Leu | Asn | Ser | Ser | Ala | Met | Met | Thr | Ser | Glu | Asn | Met | Leu |  |
|   |   |   | 755 |   |   |   |   | 760 |   |   |   |   | 765 |   |   |  |

| GAC | AGA | ATT | GCT | GGA | GGT | GAT | CTT | GAG | TCG | TCA | GTA | GAT | GAC | CCC | CGT | 2352 |
|---|---|---|---|---|---|---|---|---|---|---|---|---|---|---|---|---|
| Asp | Arg | Ile | Ala | Gly | Gly | Asp | Leu | Glu | Ser | Ser | Val | Asp | Asp | Pro | Arg |  |
|   |   | 770 |   |   |   |   | 775 |   |   |   |   | 780 |   |   |   |  |

| ACA | GAT | GAA | GAT | CGT | AGA | TTT | GAG | AGT | CAT | ATT | GAG | AAG | AAA | CCA | TAC | 2400 |
|---|---|---|---|---|---|---|---|---|---|---|---|---|---|---|---|---|
| Thr | Asp | Glu | Asp | Arg | Arg | Phe | Glu | Ser | His | Ile | Glu | Lys | Lys | Pro | Tyr |  |
|   | 785 |   |   |   |   | 790 |   |   |   |   | 795 |   |   |   |   |  |

| AAG | GAG | TTG | AGA | CTT | GAG | GTT | GGT | AAG | CAG | AGA | TTC | AAA | TAT | GCA | AGA | 2448 |
|---|---|---|---|---|---|---|---|---|---|---|---|---|---|---|---|---|
| Lys | Glu | Leu | Arg | Leu | Glu | Val | Gly | Lys | Gln | Arg | Phe | Lys | Tyr | Ala | Arg |  |
| 800 |   |   |   |   | 805 |   |   |   |   | 810 |   |   |   |   | 815 |  |

```
GAA GAA TTG TCA AAT GAG ATC TTG CCT CCC CCT AGG AAA TTG AAA GGA    2496
Glu Glu Leu Ser Asn Glu Ile Leu Pro Pro Pro Arg Lys Leu Lys Gly
            820             825             830

TTG TTT TCA CAA TCA AAA ATT TCC                                    2520
Leu Phe Ser Gln Ser Lys Ile Ser
        835
```

( 2 ) INFORMATION FOR SEQ ID NO:2:

( i ) SEQUENCE CHARACTERISTICS:
        ( A ) LENGTH: 839 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Met Ala Arg Gln Gly Leu Phe Gln Thr Val Gly Ser Gly Leu
 1               5                  10                  15

Asp His Ile Leu Ser Leu Ala Asp Val Glu Glu Gln Met Ile Gln
                20                  25                  30

Ser Val Asp Arg Thr Ala Val Thr Gly Ala Ser Tyr Phe Thr Ser Val
            35                  40                  45

Asp Gln Ser Ser Val His Thr Ala Glu Val Gly Ser His Gln Ser Glu
        50                  55                  60

Pro Leu Lys Thr Ser Val Asp Lys Pro Gly Ser Lys Lys Thr Gln Gly
65                  70                  75                  80

Glu Lys Phe Phe Leu Ile His Ser Ala Asp Trp Leu Ser Thr His Ala
                85                  90                  95

Leu Phe His Glu Val Ala Lys Leu Asp Val Val Ser Leu Leu Tyr Asn
            100                 105                 110

Glu Gln Phe Ala Val Gln Gly Leu Leu Arg Tyr His Thr Tyr Ala Arg
        115                 120                 125

Phe Gly Ile Glu Ile Gln Val Gln Ile Asn Pro Thr Pro Phe Gln Gln
    130                 135                 140

Gly Gly Leu Ile Cys Ala Met Val Pro Gly Asp Gln Gly Tyr Gly Ser
145                 150                 155                 160

Ile Ala Ser Leu Thr Val Tyr Pro His Gly Leu Leu Asn Cys Asn Ile
                165                 170                 175

Asn Asn Val Val Arg Ile Lys Val Pro Phe Ile Tyr Thr Arg Gly Ala
            180                 185                 190

Tyr His Phe Lys Asp Pro Gln Tyr Pro Val Trp Glu Leu Thr Ile Arg
        195                 200                 205

Val Trp Ser Glu Phe Asn Ile Gly Thr Gly Thr Ser Ala Tyr Thr Ser
    210                 215                 220

Leu Asn Val Leu Ala Arg Phe Thr Asp Leu Glu Leu His Gly Leu Thr
225                 230                 235                 240

Pro Leu Ser Thr Gln Met Met Arg Asn Glu Phe Arg Val Ser Thr Thr
                245                 250                 255

Glu Asn Val Val Asn Leu Ser Asn Tyr Glu Asp Ala Arg Ala Lys Met
            260                 265                 270

Ser Phe Ala Leu Asp Gln Glu Asn Trp Arg Ser Asp Pro Ser Glu Gly
        275                 280                 285

Gly Gly Ile Lys Ile Thr His Phe Ser Thr Trp Thr Ser Ile Pro Thr
    290                 295                 300

Leu Ala Ala Gln Phe Ala Phe Asn Ala Ser Ala Ser Val Gly Gln Gln
305                 310                 315                 320

Ile Lys Val Ile Pro Val Asp Pro Tyr Phe Tyr Gln Met Thr Asn Ser
```

-continued

|  |  |  | 325 |  |  |  | 330 |  |  |  | 335 |  |  |
|---|---|---|---|---|---|---|---|---|---|---|---|---|---|
| Asn | Pro | Asp | Gln<br>340 | Lys | Tyr | Ile | Thr | Ala<br>345 | Leu | Ala | Ser | Ile | Cys | Gln<br>350 | Met |
| Phe | Cys | Phe<br>355 | Trp | Arg | Gly | Asp | Leu<br>360 | Val | Phe | Asp | Phe | Gln<br>365 | Val | Phe | Pro |
| Thr | Lys<br>370 | Tyr | His | Ser | Gly | Arg<br>375 | Leu | Gln | Phe | Cys | Phe<br>380 | Val | Pro | Gly | Asn |
| Glu<br>385 | Leu | Ile | Glu | Val | Thr<br>390 | Ser | Ile | Thr | Leu | Lys<br>395 | Gln | Ala | Thr | Thr | Ala<br>400 |
| Pro | Cys | Ala | Val | Met<br>405 | Asp | Ile | Thr | Gly | Val<br>410 | Gln | Ser | Thr | Leu | Arg<br>415 | Phe |
| Arg | Val | Pro | Trp<br>420 | Ile | Ser | Asp | Thr | Pro<br>425 | Tyr | Arg | Val | Asn | Cys<br>430 | Tyr | Ile |
| Lys | Ser | Ser<br>435 | His | Gln | Lys | Gly | Glu<br>440 | Tyr | Thr | Ala | Ile | Glu<br>445 | Lys | Leu | Ile |
| Val | Tyr<br>450 | Cys | Tyr | Asn | Arg | Leu<br>455 | Thr | Ser | Pro | Ser | Asn<br>460 | Val | Ala | Ser | His |
| Val<br>465 | Arg | Val | Asn | Val | Tyr<br>470 | Leu | Ser | Ala | Ile | Asn<br>475 | Leu | Glu | Cys | Phe | Ala<br>480 |
| Pro | Leu | Tyr | His | Ala<br>485 | Met | Asp | Val | Thr | Ser<br>490 | Gln | Thr | Gly | Asp | Asp<br>495 | Ser |
| Gly | Gly | Phe | Ser<br>500 | Thr | Thr | Val | Ser | Thr<br>505 | Glu | Gln | Asn | Val | Pro<br>510 | Asp | Pro |
| Gln | Val | Gly<br>515 | Ile | Thr | Thr | Pro | Lys<br>520 | Asp | Leu | Lys | Gly | Lys<br>525 | Ala | Asn | Lys |
| Gly | Lys<br>530 | Met | Asp | Val | Ser | Gly<br>535 | Val | Gln | Ala | Pro | Val<br>540 | Gly | Ala | Ile | Thr |
| Thr<br>545 | Ile | Glu | Asp | Pro | Val<br>550 | Leu | Ala | Lys | Lys | Val<br>555 | Pro | Glu | Thr | Phe | Pro<br>560 |
| Glu | Leu | Lys | Pro | Gly<br>565 | Glu | Ser | Arg | His | Thr<br>570 | Ser | Asp | His | Met | Ser<br>575 | Val |
| Tyr | Lys | Phe | Met<br>580 | Gly | Arg | Ser | His | Phe<br>585 | Leu | Cys | Thr | Phe | Thr<br>590 | Phe | Asn |
| Ala | Asn | Asn<br>595 | Arg | Glu | Tyr | Thr | Phe<br>600 | Pro | Ile | Thr | Leu | Ser<br>605 | Ser | Thr | Ser |
| Asn | Pro<br>610 | Pro | His | Gly | Ser | Pro<br>615 | Ser | Thr | Leu | Arg | Trp<br>620 | Phe | Phe | Asn | Leu |
| Phe<br>625 | Gln | Leu | Tyr | Arg | Gly<br>630 | Pro | Leu | Asp | Leu | Thr<br>635 | Ile | Ile | Ile | Thr | Gly<br>640 |
| Ala | Thr | Asp | Val | Asp<br>645 | Gly | Met | Ala | Trp | Phe<br>650 | Thr | Pro | Val | Gly | Leu<br>655 | Ala |
| Val | Asp | Thr | Pro<br>660 | Trp | Val | Glu | Lys | Gln<br>665 | Ser | Ala | Leu | Thr | Ile<br>670 | Asp | Tyr |
| Lys | Thr | Ala<br>675 | Leu | Gly | Ala | Ile | Arg<br>680 | Phe | Asn | Thr | Arg | Arg<br>685 | Thr | Gly | Asn |
| Ile | Gln<br>690 | Ile | Arg | Leu | Pro | Trp<br>695 | Tyr | Ser | Tyr | Leu | Tyr<br>700 | Ala | Val | Ser | Gly |
| Ala<br>705 | Leu | Asp | Gly | Leu | Gly<br>710 | Asp | Thr | Thr | Asp | Ser<br>715 | Thr | Phe | Gly | Leu | Val<br>720 |
| Ser | Ile | Gln | Ile | Ala<br>725 | Asn | Tyr | Asn | His | Ser<br>730 | Asp | Glu | Tyr | Leu | Ser<br>735 | Phe |
| Ser | Cys | Tyr | Leu<br>740 | Ser | Val | Thr | Glu | Gln<br>745 | Ser | Glu | Phe | Phe | Phe<br>750 | Pro | Arg |
| Ala | Pro | Leu | Asn<br>755 | Ser | Ser | Ala | Met | Met<br>760 | Thr | Ser | Glu | Asn | Met<br>765 | Leu | Asp |

| | | | | | | | | | | | | | | |
|---|---|---|---|---|---|---|---|---|---|---|---|---|---|---|
| Arg | Ile | Ala | Gly | Gly | Asp | Leu | Glu | Ser | Ser | Val | Asp | Asp | Pro | Arg | Thr |
| | 770 | | | | 775 | | | | | 780 | | | | | |
| Asp | Glu | Asp | Arg | Arg | Phe | Glu | Ser | His | Ile | Glu | Lys | Lys | Pro | Tyr | Lys |
| 785 | | | | | 790 | | | | | 795 | | | | | 800 |
| Glu | Leu | Arg | Leu | Glu | Val | Gly | Lys | Gln | Arg | Phe | Lys | Tyr | Ala | Arg | Glu |
| | | | | 805 | | | | | 810 | | | | | 815 | |
| Glu | Leu | Ser | Asn | Glu | Ile | Leu | Pro | Pro | Pro | Arg | Lys | Leu | Lys | Gly | Leu |
| | | | 820 | | | | | 825 | | | | | 830 | | |
| Phe | Ser | Gln | Ser | Lys | Ile | Ser |
| | | 835 | | | | |

(2) INFORMATION FOR SEQ ID NO:3:

(i) SEQUENCE CHARACTERISTICS:
      (A) LENGTH: 486 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 1..486

(xi) SEQUENCE DESCRIPTION: SEQ ID NO:3:

```
GGT TTA TTA AAT TGC AAT ATT AAC AAT GTA GTA AGA ATC AAG TTC CCT      48
Gly Leu Leu Asn Cys Asn Ile Asn Asn Val Val Arg Ile Lys Phe Pro
  1               5                  10                  15

TTC ATT TAT ACT AGA GGT GCT TAT CAT TTT AAA GAT CCA CAG TAT CCA      96
Phe Ile Tyr Thr Arg Gly Ala Tyr His Phe Lys Asp Pro Gln Tyr Pro
             20                  25                  30

GTC TGG GAA CTT ACA ATT CGT GTG TGG TCT GAG CTC AAT ATT GGA ACT     144
Val Trp Glu Leu Thr Ile Arg Val Trp Ser Glu Leu Asn Ile Gly Thr
         35                  40                  45

GGT ACT TCT GCA TAT ACA TCT TTA AAT GTG CTT GCT AGA TTT ACA GAT     192
Gly Thr Ser Ala Tyr Thr Ser Leu Asn Val Leu Ala Arg Phe Thr Asp
     50                  55                  60

TTG GAG TTG CAT GGC TTG ACT CCA TTG TCT ACT CAG ATG ATG AGA AAT     240
Leu Glu Leu His Gly Leu Thr Pro Leu Ser Thr Gln Met Met Arg Asn
 65                  70                  75                  80

GAA TTT AGA GTT AGT ACA ACT GAG AAT GTA GTT AAT TTG TCC AAT TAT     288
Glu Phe Arg Val Ser Thr Thr Glu Asn Val Val Asn Leu Ser Asn Tyr
                 85                  90                  95

GAG GAT GCT AGA GCA AAA ATG TCA TTT GCT CTG GAT CAA GAG GAT TGG     336
Glu Asp Ala Arg Ala Lys Met Ser Phe Ala Leu Asp Gln Glu Asp Trp
             100                 105                 110

AAA TCT GAT CCA TCC CAG GGA GGT GGA GTT AAA ATC ACT CAT TTC ACA     384
Lys Ser Asp Pro Ser Gln Gly Gly Gly Val Lys Ile Thr His Phe Thr
         115                 120                 125

ACA TGG ACC TCA ATT CCC ACT TTG GCT GCT CAA TTT GCT TTT AAT GCT     432
Thr Trp Thr Ser Ile Pro Thr Leu Ala Ala Gln Phe Ala Phe Asn Ala
     130                 135                 140

TCA GCT TCT GTG GGA CAA CAA ATT AAG GTT ATT CCT GTT GAT CCT TAT     480
Ser Ala Ser Val Gly Gln Gln Ile Lys Val Ile Pro Val Asp Pro Tyr
145                 150                 155                 160

TTT TAT                                                              486
Phe Tyr
```

(2) INFORMATION FOR SEQ ID NO:4:

(i) SEQUENCE CHARACTERISTICS:
      (A) LENGTH: 162 amino acids
      (B) TYPE: amino acid
      (D) TOPOLOGY: linear ( i i ) MOLECULE TYPE: protein ( x i ) SEQUENCE DESCRIPTION: SEQ ID NO:4:

| Gly | Leu | Leu | Asn | Cys | Asn | Ile | Asn | Asn | Val | Val | Arg | Ile | Lys | Phe | Pro |
|---|---|---|---|---|---|---|---|---|---|---|---|---|---|---|---|
| 1 | | | | 5 | | | | | 10 | | | | | 15 | |

| Phe | Ile | Tyr | Thr | Arg | Gly | Ala | Tyr | His | Phe | Lys | Asp | Pro | Gln | Tyr | Pro |
|---|---|---|---|---|---|---|---|---|---|---|---|---|---|---|---|
| | | | 20 | | | | | 25 | | | | | 30 | | |

| Val | Trp | Glu | Leu | Thr | Ile | Arg | Val | Trp | Ser | Glu | Leu | Asn | Ile | Gly | Thr |
|---|---|---|---|---|---|---|---|---|---|---|---|---|---|---|---|
| | | 35 | | | | | 40 | | | | | 45 | | | |

| Gly | Thr | Ser | Ala | Tyr | Thr | Ser | Leu | Asn | Val | Leu | Ala | Arg | Phe | Thr | Asp |
|---|---|---|---|---|---|---|---|---|---|---|---|---|---|---|---|
| | 50 | | | | | 55 | | | | | 60 | | | | |

| Leu | Glu | Leu | His | Gly | Leu | Thr | Pro | Leu | Ser | Thr | Gln | Met | Met | Arg | Asn |
|---|---|---|---|---|---|---|---|---|---|---|---|---|---|---|---|
| 65 | | | | | 70 | | | | | 75 | | | | | 80 |

| Glu | Phe | Arg | Val | Ser | Thr | Thr | Glu | Asn | Val | Val | Asn | Leu | Ser | Asn | Tyr |
|---|---|---|---|---|---|---|---|---|---|---|---|---|---|---|---|
| | | | | 85 | | | | | 90 | | | | | 95 | |

| Glu | Asp | Ala | Arg | Ala | Lys | Met | Ser | Phe | Ala | Leu | Asp | Gln | Glu | Asp | Trp |
|---|---|---|---|---|---|---|---|---|---|---|---|---|---|---|---|
| | | | 100 | | | | | 105 | | | | | 110 | | |

| Lys | Ser | Asp | Pro | Ser | Gln | Gly | Gly | Val | Lys | Ile | Thr | His | Phe | Thr |
|---|---|---|---|---|---|---|---|---|---|---|---|---|---|---|
| | | 115 | | | | | 120 | | | | | 125 | | |

| Thr | Trp | Thr | Ser | Ile | Pro | Thr | Leu | Ala | Ala | Gln | Phe | Ala | Phe | Asn | Ala |
|---|---|---|---|---|---|---|---|---|---|---|---|---|---|---|---|
| | 130 | | | | | 135 | | | | | 140 | | | | |

| Ser | Ala | Ser | Val | Gly | Gln | Gln | Ile | Lys | Val | Ile | Pro | Val | Asp | Pro | Tyr |
|---|---|---|---|---|---|---|---|---|---|---|---|---|---|---|---|
| 145 | | | | | 150 | | | | | 155 | | | | | 160 |

Phe Tyr ( 2 ) INFORMATION FOR SEQ ID NO:5:

( i ) SEQUENCE CHARACTERISTICS:
      ( A ) LENGTH: 668 base pairs
      ( B ) TYPE: nucleic acid
      ( C ) STRANDEDNESS: double
      ( D ) TOPOLOGY: linear ( i x ) FEATURE:
      ( A ) NAME/KEY: CDS
      ( B ) LOCATION: 3..668

( x i ) SEQUENCE DESCRIPTION: SEQ ID NO:5:

| AT | GCT | ATG | GAT | GTT | ACA | TCC | CAG | ACA | GGA | GAT | GAT | TCT | GGA | GGT | TTT | 47 |
|---|---|---|---|---|---|---|---|---|---|---|---|---|---|---|---|---|
| | Ala | Met | Asp | Val | Thr | Ser | Gln | Thr | Gly | Asp | Asp | Ser | Gly | Gly | Phe | |
| | 1 | | | | 5 | | | | | 10 | | | | | 15 | |

| TCA | ACT | ACA | GTT | TCT | ACT | GAA | CAG | AAT | GCT | CCT | GAT | CCT | CAG | GTT | GGT | 95 |
|---|---|---|---|---|---|---|---|---|---|---|---|---|---|---|---|---|
| Ser | Thr | Thr | Val | Ser | Thr | Glu | Gln | Asn | Ala | Pro | Asp | Pro | Gln | Val | Gly | |
| | | | | 20 | | | | | 25 | | | | | 30 | | |

| ATT | ACA | ACA | ATC | AAG | GAT | TTG | AAA | GGG | AAA | GCA | AAT | AGA | GGA | AAA | ATG | 143 |
|---|---|---|---|---|---|---|---|---|---|---|---|---|---|---|---|---|
| Ile | Thr | Thr | Ile | Lys | Asp | Leu | Lys | Gly | Lys | Ala | Asn | Arg | Gly | Lys | Met | |
| | | | 35 | | | | | 40 | | | | | 45 | | | |

| GAT | GTT | TCT | GGC | GTC | CAA | GCT | CCA | GTT | GGT | GCT | ATC | ACA | ACT | ATA | GAA | 191 |
|---|---|---|---|---|---|---|---|---|---|---|---|---|---|---|---|---|
| Asp | Val | Ser | Gly | Val | Gln | Ala | Pro | Val | Gly | Ala | Ile | Thr | Thr | Ile | Glu | |
| | | 50 | | | | | 55 | | | | | 60 | | | | |

| GAT | CCA | GTG | TTA | GCC | AAG | AAA | ATT | CCT | GAA | ACA | TTT | CCA | GAG | TTG | AAG | 239 |
|---|---|---|---|---|---|---|---|---|---|---|---|---|---|---|---|---|
| Asp | Pro | Val | Leu | Ala | Lys | Lys | Ile | Pro | Glu | Thr | Phe | Pro | Glu | Leu | Lys | |
| | 65 | | | | | 70 | | | | | 75 | | | | | |

| CCA | GGT | GAG | TCT | AGA | CAT | ACA | TCA | GAT | CAT | ATG | TCT | ATT | TAC | AAA | TTT | 287 |
|---|---|---|---|---|---|---|---|---|---|---|---|---|---|---|---|---|
| Pro | Gly | Glu | Ser | Arg | His | Thr | Ser | Asp | His | Met | Ser | Ile | Tyr | Lys | Phe | |
| 80 | | | | | 85 | | | | | 90 | | | | | 95 | |

| ATG | GGC | AGG | TCA | CAC | TTT | TTG | TGT | ACT | TTC | ACT | TTT | AAT | GCA | AAC | AAT | 335 |
|---|---|---|---|---|---|---|---|---|---|---|---|---|---|---|---|---|
| Met | Gly | Arg | Ser | His | Phe | Leu | Cys | Thr | Phe | Thr | Phe | Asn | Ala | Asn | Asn | |
| | | | 100 | | | | | 105 | | | | | 110 | | | |

| AGA | GAA | TAT | ACC | TTT | CCA | ATA | ACT | TTG | TCT | TCA | ACA | TCT | AAT | CCT | CCC | 383 |
|---|---|---|---|---|---|---|---|---|---|---|---|---|---|---|---|---|
| Arg | Glu | Tyr | Thr | Phe | Pro | Ile | Thr | Leu | Ser | Ser | Thr | Ser | Asn | Pro | Pro | |
| | | | 115 | | | | | 120 | | | | | 125 | | | |

| | | | | | | | | | | | | | | | | |
|---|---|---|---|---|---|---|---|---|---|---|---|---|---|---|---|---|
| CAT | GGT | TTG | CCA | TCA | ACT | TTA | CGG | TGG | TTC | TTT | AAT | CTG | TTT | CAG | CTG | 431 |
| His | Gly | Leu | Pro | Ser | Thr | Leu | Arg | Trp | Phe | Phe | Asn | Leu | Phe | Gln | Leu | |
| | | 130 | | | | 135 | | | | | 140 | | | | | |
| TAT | AGA | GGA | CCA | CTG | GAT | TTG | ACT | ATT | ATT | ATC | ACA | GGA | GCC | ACT | GAT | 479 |
| Tyr | Arg | Gly | Pro | Leu | Asp | Leu | Thr | Ile | Ile | Ile | Thr | Gly | Ala | Thr | Asp | |
| | 145 | | | | 150 | | | | | 155 | | | | | | |
| GTT | GAT | GGG | ATG | GCT | TGG | TTC | ACC | CCT | GTG | GGT | CTT | GCC | GTT | GAC | ACT | 527 |
| Val | Asp | Gly | Met | Ala | Trp | Phe | Thr | Pro | Val | Gly | Leu | Ala | Val | Asp | Thr | |
| 160 | | | | | 165 | | | | | 170 | | | | | 175 | |
| CCT | TGG | GTG | GAA | AAG | CAG | TCA | GCT | TTA | ACT | ATT | GAT | TAT | AAG | ACA | GCA | 575 |
| Pro | Trp | Val | Glu | Lys | Gln | Ser | Ala | Leu | Thr | Ile | Asp | Tyr | Lys | Thr | Ala | |
| | | | | 180 | | | | | 185 | | | | | 190 | | |
| TTG | GGG | GCT | ATT | AGT | TTT | AAT | ACC | AGA | AGA | ACT | GGC | AAC | ATT | CAA | ATT | 623 |
| Leu | Gly | Ala | Ile | Ser | Phe | Asn | Thr | Arg | Arg | Thr | Gly | Asn | Ile | Gln | Ile | |
| | | | 195 | | | | | 200 | | | | | 205 | | | |
| AGA | CTT | CCG | TGG | TAT | TCA | TAT | CTT | TAT | GCT | GTG | TCT | GGC | GCC | CTA | | 668 |
| Arg | Leu | Pro | Trp | Tyr | Ser | Tyr | Leu | Tyr | Ala | Val | Ser | Gly | Ala | Leu | | |
| | | 210 | | | | | 215 | | | | | 220 | | | | |

(2) INFORMATION FOR SEQ ID NO:6:

(i) SEQUENCE CHARACTERISTICS:
(A) LENGTH: 222 amino acids
(B) TYPE: amino acid
(D) TOPOLOGY: linear (ii) MOLECULE TYPE: protein (xi) SEQUENCE DESCRIPTION: SEQ ID NO:6:

| Ala | Met | Asp | Val | Thr | Ser | Gln | Thr | Gly | Asp | Asp | Ser | Gly | Gly | Phe | Ser |
|---|---|---|---|---|---|---|---|---|---|---|---|---|---|---|---|
| 1 | | | | 5 | | | | | 10 | | | | | 15 | |
| Thr | Thr | Val | Ser | Thr | Glu | Gln | Asn | Ala | Pro | Asp | Pro | Gln | Val | Gly | Ile |
| | | | 20 | | | | | 25 | | | | | 30 | | |
| Thr | Thr | Ile | Lys | Asp | Leu | Lys | Gly | Lys | Ala | Asn | Arg | Gly | Lys | Met | Asp |
| | | | 35 | | | | 40 | | | | | 45 | | | |
| Val | Ser | Gly | Val | Gln | Ala | Pro | Val | Gly | Ala | Ile | Thr | Thr | Ile | Glu | Asp |
| | 50 | | | | | 55 | | | | | 60 | | | | |
| Pro | Val | Leu | Ala | Lys | Lys | Ile | Pro | Glu | Thr | Phe | Pro | Glu | Leu | Lys | Pro |
| 65 | | | | | 70 | | | | | 75 | | | | | 80 |
| Gly | Glu | Ser | Arg | His | Thr | Ser | Asp | His | Met | Ser | Ile | Tyr | Lys | Phe | Met |
| | | | | 85 | | | | | 90 | | | | | 95 | |
| Gly | Arg | Ser | His | Phe | Leu | Cys | Thr | Phe | Thr | Phe | Asn | Ala | Asn | Asn | Arg |
| | | | 100 | | | | | 105 | | | | | 110 | | |
| Glu | Tyr | Thr | Phe | Pro | Ile | Thr | Leu | Ser | Ser | Thr | Ser | Asn | Pro | Pro | His |
| | | 115 | | | | | 120 | | | | | 125 | | | |
| Gly | Leu | Pro | Ser | Thr | Leu | Arg | Trp | Phe | Phe | Asn | Leu | Phe | Gln | Leu | Tyr |
| | 130 | | | | | 135 | | | | | 140 | | | | |
| Arg | Gly | Pro | Leu | Asp | Leu | Thr | Ile | Ile | Ile | Thr | Gly | Ala | Thr | Asp | Val |
| 145 | | | | | 150 | | | | | 155 | | | | | 160 |
| Asp | Gly | Met | Ala | Trp | Phe | Thr | Pro | Val | Gly | Leu | Ala | Val | Asp | Thr | Pro |
| | | | | 165 | | | | | 170 | | | | | 175 | |
| Trp | Val | Glu | Lys | Gln | Ser | Ala | Leu | Thr | Ile | Asp | Tyr | Lys | Thr | Ala | Leu |
| | | | 180 | | | | | 185 | | | | | 190 | | |
| Gly | Ala | Ile | Ser | Phe | Asn | Thr | Arg | Arg | Thr | Gly | Asn | Ile | Gln | Ile | Arg |
| | | | 195 | | | | | 200 | | | | | 205 | | |
| Leu | Pro | Trp | Tyr | Ser | Tyr | Leu | Tyr | Ala | Val | Ser | Gly | Ala | Leu | | |
| | 210 | | | | | 215 | | | | | 220 | | | | |

DNA SEQUENCE ENCODING A CYNOMOLGUS MONKEY HEPATITIS A VIRUS CAPSID PROTEIN

This is a continuation of application Ser. No. 07/678,828, filed Apr. 3, 1991, now abandoned.

BACKGROUND OF THE INVENTION

1. Field of the Invention

The present invention relates, in general, to hepatitis A viruses. In particular, the present invention relates to cynomolgus monkey hepatitis A viruses and vaccines containing same.

2. Background Information

Humans have been considered the natural host for hepatitis A virus (HAV), although nonhuman primates can be infected experimentally (Dienstag, J. L., et al. (1975) Journal of Infectious Diseases 132, 532–545). Human HAV is a single serotype and different isolates have shown a high degree of nucleotide and amino acid conservation. HAV infections in wild-caught Panamanian owl monkeys (*Aotus trivireatus*) have been thought to be caused by a host-specific HAV, designated PA 21 (Brown, E. A., et al. (1989) Journal of Virology 63, 4932–4937). Although the nucleic acid sequence of the capsid region of PA 21 differs by more than 17% from most of the sequenced human HAV isolates, this genotype has now been identified in patients with hepatitis A (Jansen, R. W., et al, (1990) Proc. Natl. Acad. Sci. USA 87, 2867–2871; Robertson, B. H., et al. (1991) Journal of Infectious Diseases 163, 286–292).

Antibody to HAV has been detected in newly captured cynomolgus macaques (*Macaca fascicularis*) and was thought to be the result of infection with human HAV (Burke, D. S., et al. (1984) American Journal of Tropical Medicine and Hygiene 33, 940–944). The present invention provides the sequence of the capsid region of HAV isolated from cynomolgus monkeys (cyno-HAV) and demonstrates that it is divergent from other HAV isolates and contains significant amino acid changes within the putative immunodominant site.

SUMMARY OF THE INVENTION

It is a general object of this invention to provide a hepatitis A viral isolate.

It is a specific object of this invention to provide the cynomolgus hepatitis A viral isolates CY-145 and CY-55/JM-55.

It is another object of the invention to provide cDNAs of the genomic RNA of the cynomolgus hepatitis A viral isolates CY-145 and CY-55/JM-55.

It is another object of the invention to provide a method of preventing hepatitis A in an animal.

It is a further object of the invention to provide vaccines comprising the cynomolgus hepatitis A viral isolates CY-145 and CY-55/JM-55.

Further objects and advantages of the present invention will be clear from the description that follows.

BRIEF DESCRIPTION OF THE DRAWINGS

FIG. 3. Nucleotide (SEQ ID NO:1) and predicted amino acid (SEQ ID NO:2) sequence of the capsid region of CY-145. The right angle arrows indicate cleavage sites of capsid polyproteins. Straight arrow indicates position of three nucleotide deletion, relative to human HAV, at 5' end of P2 region. A partial sequence for the CY-55/JM-55 capsid region is shown above (nucleotides) (SEQ ID NO:3 and SEQ ID NO:5) or below (amino acids) the CY-145 sequence. Asterisks indicate amino acids involved in the proposed immunodominant site. Dots indicate identical sequence and changes are indicated by the appropriate letter code.

DETAILED DESCRIPTION OF THE INVENTION

Figure 1:
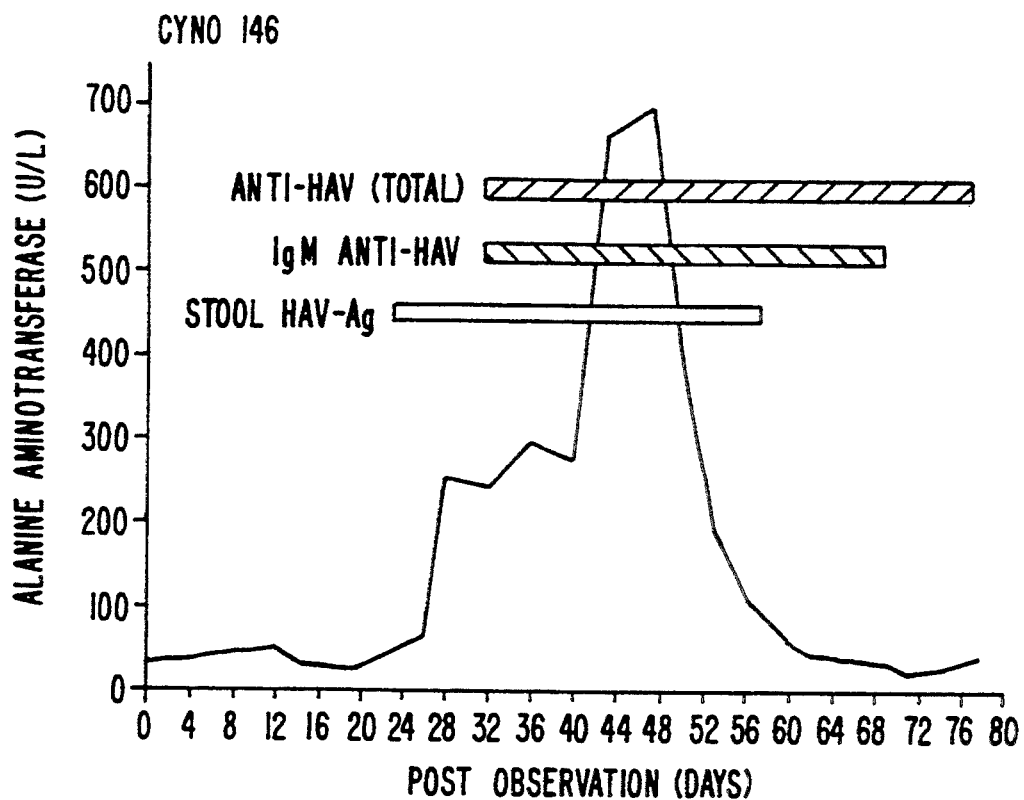
FIG. 1. Events during natural infection with cynomolgus HAV. Animal CY 146 was representative of all infections (animal CY 145 was sacrificed at peak of ALT elevation). Alanine amino-transferase (ALT) was determined colorimetrically. Antibody to HAV and IgM antibody to HAV were detected by enzyme immunoassay (HAVAB and HAVAB-M, Abbott Laboratories, N. Chicago, Ill.). HAV antigen in stool was detected by enzyme immunoassay (Margolis, H. S. & Nainan, O. V. (1990) Hepatology 11, 31–37).
Figure 2:
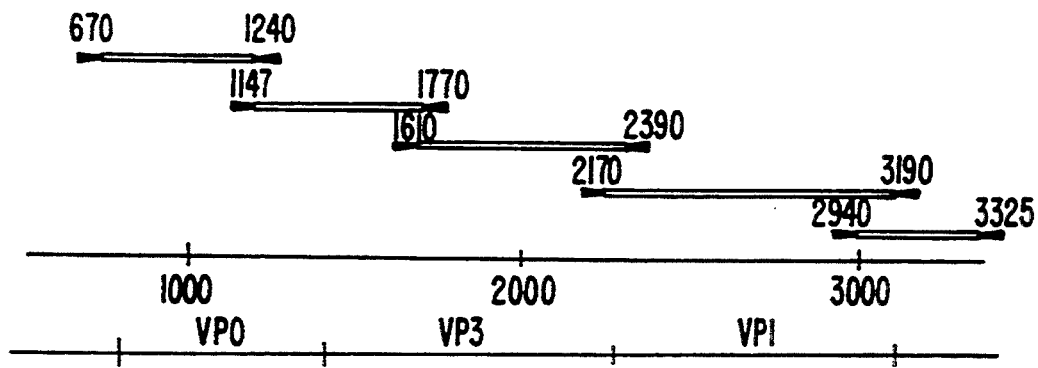
FIG. 2. Strategy for sequencing the capsid region of CY-145 by using PCR generated overlapping fragments. Twenty to 25-mer forward and reverse primers are indicated by arrows. The numbers above the arrows indicate the start of each PCR fragment relative to the human HAV genome (Cohen, J. I. et al. (1987) Proc. Natl. Acad. Sci. USA 84, 2497–2501). Primer sequences were derived from the consensus sequence for human HAV using the computer algorithm described by Devereux, J., et al. ((1983) Nucleic Acids Research 12, 387–395).

The present invention relates to a cynomolgus hepatitis A viral isolate.

In one embodiment, the present invention relates to substantially pure preparations of viral isolates having the characteristics of cynomolgus hepatitis A viral isolates CY-145 and CY-55/JM-55. The preferred isolates were immunocaptured in microfuge tubes coated with polyclonal rabbit anti-human-HAV and shown to be substantially free of contaminating viruses. The immunocaptured virus is free of any other contaminating viruses, since the antibody is specific for hepatitis A virus.

In another embodiment, the present invention relates to cDNAs of the genomic RNA of cynomolgus hepatitis A viral isolates having the characteristics of CY-145 and CY-55/JM-55. In one preferred embodiment, the cDNAs have the sequences shown in FIG. 3, or portions thereof encoding viral antigens.

In another embodiment, the present invention relates to a method of preventing hepatitis A in an animal. The method comprises administering to the animal the above-described hepatitis A viral isolate, preferably CY-145 or CY-55/JM-55, under conditions such that hepatitis A is prevented. The virus prior to use may be adapted in a cell-line suitable for human vaccine development thus producing a whole virus vaccine that could be either live attenuated or inactivated. Additionally, if cloned into an expression vector, the cDNA coding for the capsid region of the virus may provide virus-like antigen which could substitute for the whole virus. One skilled in the art will appreciate that the amounts to be administered for any particular treatment protocol can readily be determined. Animals suitable for use in the claimed method include humans and chimpanzees.

In a further embodiment, the present invention relates to a vaccine comprising the above-described hepatitis A viral isolate CY-145 or CY-55/JM-55 in an amount effective to prevent hepatitis A in an animal and a pharmaceutically acceptable diluent, carrier, or excipient. The preferred vaccine of the invention includes the viral isolate CY-145 or CY-55/JM-55 in a quantity selected depending on the route of administration (preferably, intramuscular (I.M.)). Appropriate concentrations and dosage unit sizes can be readily determined by one skilled in the art. Suitable amounts might be expected to fall within the range of approximately $10^7$ to approximately $10^8$ viral particles. Given the sequence and the viruses described, one skilled in the art could clone and express the antigenic regions of these hepatitis viruses for the purpose of vaccine development. Additionally, the hepatitis A viral isolates CY-145 or CY-55/JM-55 can be used in genetically engineered chimeric vaccines.

The present invention is described in further detail in the following non-limiting examples.

EXAMPLE 1

Isolation and Characterization of a Hepatitis A Virus

Cyno-HAV, isolated from two different sources, was used in this study. One isolate (CY-145) was obtained from the stool of an animal with serologically and histologically confirmed spontaneous hepatitis A (FIG. 1). This animal was one of a group of six animals that contracted disease in quarantine after being imported from the Philippines. A second isolate came from the stool of a cynomolgus macaque inoculated intravenously with a 10% liver homogenate obtained from a macaque imported from Indonesia (JM-55/CY-55) that spontaneously developed HAV infection (Andjarparidze, A. G., et al. (1985) Voprosy Virusologii 4, 468–474).

Cyno-HAV was immunocaptured in microfuge tubes coated with polyclonal rabbit anti-human-HAV, as previously described (Robertson, B.H., et al. (1991) Journal of Infectious Diseases 163, 286–292). Viral RNA for amplification by polymerase chain reaction (PCR) was isolated by digestion with proteinase K (2 mg/ml, Boehringer Mannheim, Indianapolis, Ind.) in 20 mM Tris, pH 7.5, containing 10 mM EDTA, 0.1% SDS, and 1% vanadyl-ribonucleoside complexes at 42° C. for 1 hr, using beta-globin mRNA (BRL, Gaithersburg, Md.) as a carrier, followed by serial extraction with phenol-chloroform and chloroform and ethanol precipitation. The RNA was resuspended in 50% DMSO, incubated at 60° C. for 25 min before annealing with an appropriate oligonucleotide primer at 65° C. for 15 min, and reverse transcribed, as described previously (Margolis, H.S. & Nainan, O.V. (1990) Hepatology 11, 31–37; Robertson, B. H., et al. (1991) Journal of Infectious Diseases 163, 286–292). The resulting cDNA was ethanol precipitated, resuspended in PCR buffer containing the amplification primers, dNTP's and Taq polymerase, and amplified for 30 cycles using optimal conditions calculated according to the primer's $T_m$ and the expected length of the amplified fragment (FIG. 2).

PCR products were purified on a 4.5% acrylamide gel. DNA from ethidium bromide-stained bands of the appropriate size was eluted as described (Maniatis, T., et al. (1989) Molecular cloning: A laboratory manual. Cold Spring Harbor Laboratory, Cold Spring Harbor, N.Y.). The eluted samples were passed through spinnex columns (Costar, Cambridge, Mass.) to remove residual polyacrylamide. DNA was purified by serial phenol-chloroform and chloroform extraction, ethanol precipitated, and resuspended in TE buffer (10 mM Tris, 1 mM EDTA, pH 8) and quantitated by the DNA dipstick method (Invitrogen, San Diego, Calif.).

Double-stranded PCR products were sequenced using a modification of the dideoxy chain termination method (Sanger, F., et al. (1977) Proc. Natl. Acad. Sci. USA 74, 5463–5467; Winship, P. (1989) Nucleic Acids Research 17, 1266). Purified PCR-DNA and primer (10–20 pmoles) were dried with 10 μCi $35_S$ dATP (Amersham), and the sequencing reaction was done using Sequenase (Sequenase kit, USB, Cleveland, Ohio). Single-strand binding protein (0.5 μg, USB) was added to the annealed template-primer mixture, and concentrations of nucleotides were reduced sixfold from those described in the original procedure (Winship, p. (1989) Nucleic Acids Research 17, 1266). After the reaction was stopped, the samples were treated with proteinase K as described previously (Robertson, B. H., et al. (1991) Journal of Infectious Diseases 163, 286–292). Samples were denatured at 78° C. for 2 min and snap-cooled, and electrophoresis was performed at 1500 volts on a 6% polyacrylamide gel containing 8M urea.

Initial sequencing of each fragment was done with the primers used for PCR amplification; the sequencing of the fragment was then extended using primers derived from the sequence obtained. Fragments were amplified at least twice from viral RNA and both strands of amplified DNA were sequenced. The complete sequence of the capsid region of CY-145 and a partial sequence of this region of JM-55/CY-55 are shown in FIG. 3. The nucleic acid sequence was analyzed using computer algorithms provided by the Genetics Computer Group, University of Wisconsin (Devereux, J., et al. (1983) Nucleic Acids Research 12, 387–395). When compared with human HAV isolates, no insertions or deletions were present in the capsid region of the cyno isolates. CY-145 differs in 446 (18.8%) of the 2,373 capsid region nucleotides from the human HAV isolate HM175 (Cohen, J. I., et al. (1987) Proc. Natl. Acad. Sci. USA 84, 2497–2501). However, 370 of these changes are at the third position of a codon and do not alter the amino acid composition of the translated protein. The majority of the amino acid changes observed were located within the VP3 and VP1 proteins. Analysis of the proposed cleavage sites of the capsid proteins (Linemeyer, D. L., et al. (1985) Journal of Virology 54, 247–255; Cohen, J. I., et al. (1987) Proc. Natl. Acad. Sci. USA 84, 2497–2501) showed an amino acid substitution at the VP3-VP1 cleavage site. In all human HAV isolates sequenced to date, a Gln-Val pair is cleaved at this site, where as in cyno isolates, the valine is replaced by threonine. The amino acid composition of this cleavage site is analogous to that of foot and mouth disease virus (Strohmaier, K., et al. (1978) Biochem. Biophys. Res. Comm. 85, 1640–1645). The other two cleavage sites of the capsid protein of CY-145 are identical to those in human HAV. A three-nucleotide deletion was observed near the 5' end of the CY-145 nonstructural region (FIG. 3).

A comparison of amino acid and nucleotide identity between the capsid region of CY-145 and other HAV isolates is shown in Table 1. All human HAV isolates diverge from each other by 5.12% in the nucleotide sequence of the capsid region and have only one to three amino acid changes (Robertson, B. H., et al. (1988) In: Viral Hepatitis and Liver Disease, pp. 48–54, ed. A. J. Zuckermann, Alan R. Liss, N.Y.). The putative new world monkey isolate PA 21 diverges from human isolates by about 17% at the nucleotide level and by 2.9–3.8% at the amino acid level (Brown, E. A., et al. (1989) Journal of Virology 63, 4932–4937). However, PA 21 is serotypically identical to human HAV, since all monoclonal antibodies to human HAV tested have been shown to bind to this isolate (Brown, E. A., et al. (1989) Journal of Virology 63, 4932–4937). The nucleotide sequence of the VP3 and VP1 region of CY-145 differs from all sequenced HAV strains by 18–20%, and by more than 7% at the amino acid level. The partial sequence of the Indonesian isolate (CY-55/JM-55) showed an 18% nucleotide variation and a 3.4% amino acid variation when compared with other HAV strains, including CY-145.

Some of the amino acid changes common to CY-145 and CY-55/JM-55 appear important to the final antigenic structure as defined by binding to neutralizing monoclonal antibodies raised against human HAV. Antibody binding was assessed by enzyme immunoassay using microtiter wells (Immulon II, Dynatech, Arlington, Va.) coated with monoclonal antibody; biotinylated anti-HAV IgG (chimpanzee) and strepavidin HRP were used as the detector. Polyclonal rabbit anti-HAV showed 100% binding to human HAV (cell culture adapted strain HAS-15), CY-145 and CY-55/JM-55. HAS-15 had 95% and 72% binding, respectively, to monoclonal antibodies H7C27 (Dawson, J. G., et al. (1984) Journal of Medical Virology 14, 1–8) and K24F2 (MacGregor, A., et al. (1983) Journal of Clinical Microbiology 18, 1237–1243). However, both cyno viruses only showed a 1.4% binding to these monoclonal antibodies; findings similar to these were described by Karetnyi, Y. V., et al. (1989). Voprosy Virusolologiil, 50–53. Two amino acid residues have been identified as part of the immunodominant region in human HAV using escape mutants to monoclonal antibody K24F2 (Ping, L. H., et al. (1988) Proc. Natl. Acad. Sci. USA 85, 8281–8285). Both of these amino acids were substituted in the cyno-HAV isolates (FIG. 3). The presence of amino acid changes in the immunodominant region of cyno-HAV that are similar to those found in antibody resistant mutants suggest these changes may be responsible for the lack of monoclonal antibody binding.

Figure 4:
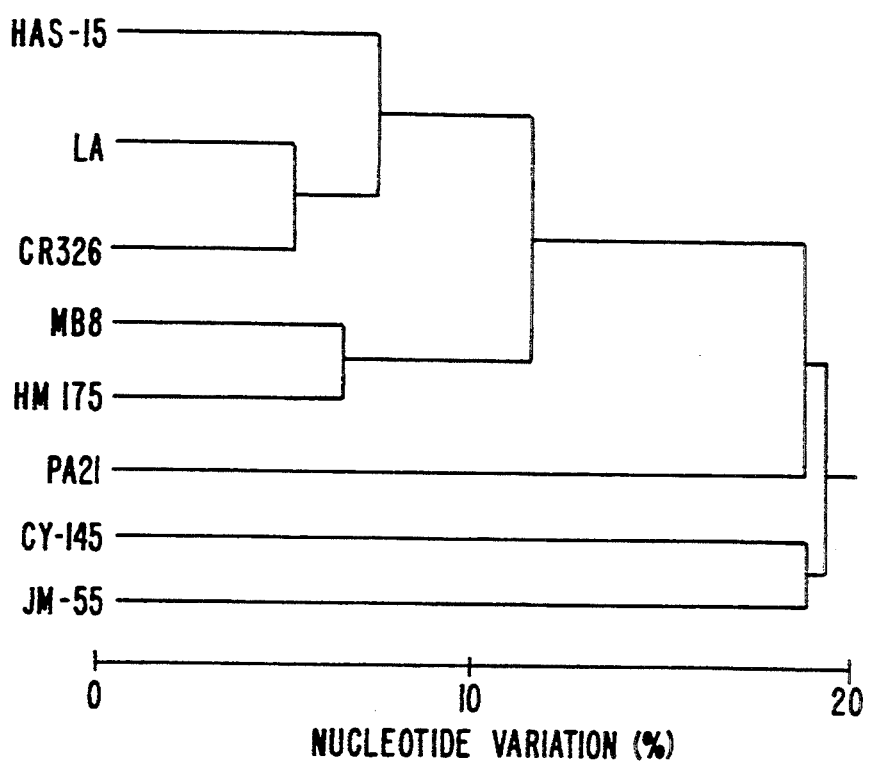
FIG. 4. Relationship among the nucleotide sequences of the capsid regions of HAV isolates obtained by pairwise analysis. The percentage variation is the horizontal distance connecting any two isolates. Human isolates are indicated by dark lines, and simian isolates are indicated by shaded lines.

Pairwise comparisons (Rico Hesse, R., et al. (1987) Virology 160, 311–322) of the nucleotide sequence of the capsid regions of the cyno-HAV isolates, human isolates, and PA21 isolate are shown in FIG. 4. This analysis indicates that cyno-HAV isolates vary from each other by approximately 20%, that they vary from the majority of human isolates by about 20%, and that they vary from the PA 21 isolate by 20%. The diversity observed between the two cynomolgus monkey viruses is likely due to their geographic isolation.

In general nucleotide variation with human HAV isolates at the capsid region ranged from 5–12% except for the PA 21 isolates which have been found in the monkeys and humans. However none of the human HAV isolates, including PA21, appear to have the amino acid changes at the identified immunodominant region, and none have shown decreased binding to monoclonal antibodies. No other HAV isolates have the unique amino acid substitution at the VP3-VP1 cleavage site as the cyno isolates. The genetic and antigenic divergence of the cyno-HAV from human isolates and the genetic diversity among geographically isolated cyno HAV isolates strongly suggest that distinct simian hepatitis A viruses exist.

TABLE 1

Percentage identity in amino acid and nucleotide composition of the capsid region of human HAV isolates compared with simian HAV isolates CY-145 and PA21.

| Capsid proteins. | HM-175 | CR326 | HAS-15 | MBB | LA | PA21 | CY-145 |
|---|---|---|---|---|---|---|---|
| | | | Amino acids | | | | |
| VP0 | | | | | | | |
| CY-145 | 96.0 | 93.9 | 95.9 | 95.9 | 95.9 | 95.9 | — |
| PA21 | 98.8 | 96.0 | 96.9 | 98.8 | 96.9 | — | 95.9 |
| VP3 | | | | | | | |
| CY-145 | 92.7 | 92.7 | 93.1 | 92.7 | 93.1 | 92.3 | — |
| PA21 | 98.4 | 98.0 | 98.0 | 98.4 | 98.0 | — | 92.3 |
| VP1 | | | | | | | |
| CY-145 | 92.4 | 91.4 | 92.9 | 92.3 | 91.0 | 92.3 | — |
| PA21 | 95.3 | 95.0 | 93.3 | 95.3 | 95.3 | — | 92.3 |
| | | | Nucleotides | | | | |
| VP0 | | | | | | | |
| CY-145 | 81.6 | 81.9 | 82.4 | 81.7 | 83.1 | 81.5 | — |
| PA21 | 87.9 | 87.6 | 88.2 | 86.5 | 88.5 | — | 81.5 |
| VP3 | | | | | | | |
| CY-145 | 82.4 | 80.5 | 80.9 | 82.4 | 81.4 | 82.4 | — |
| PA21 | 84.8 | 85.2 | 84.7 | 86.0 | 85.5 | — | 82.4 |
| VP1 | | | | | | | |
| CY-145 | 79.7 | 79.7 | 79.7 | 79.3 | 78.6 | 80.3 | — |
| PA21 | 83.2 | 82.9 | 82.1 | 83.1 | 82.9 | — | 80.3 |

EXAMPLE 2

In vivo Studies

Figure 5:
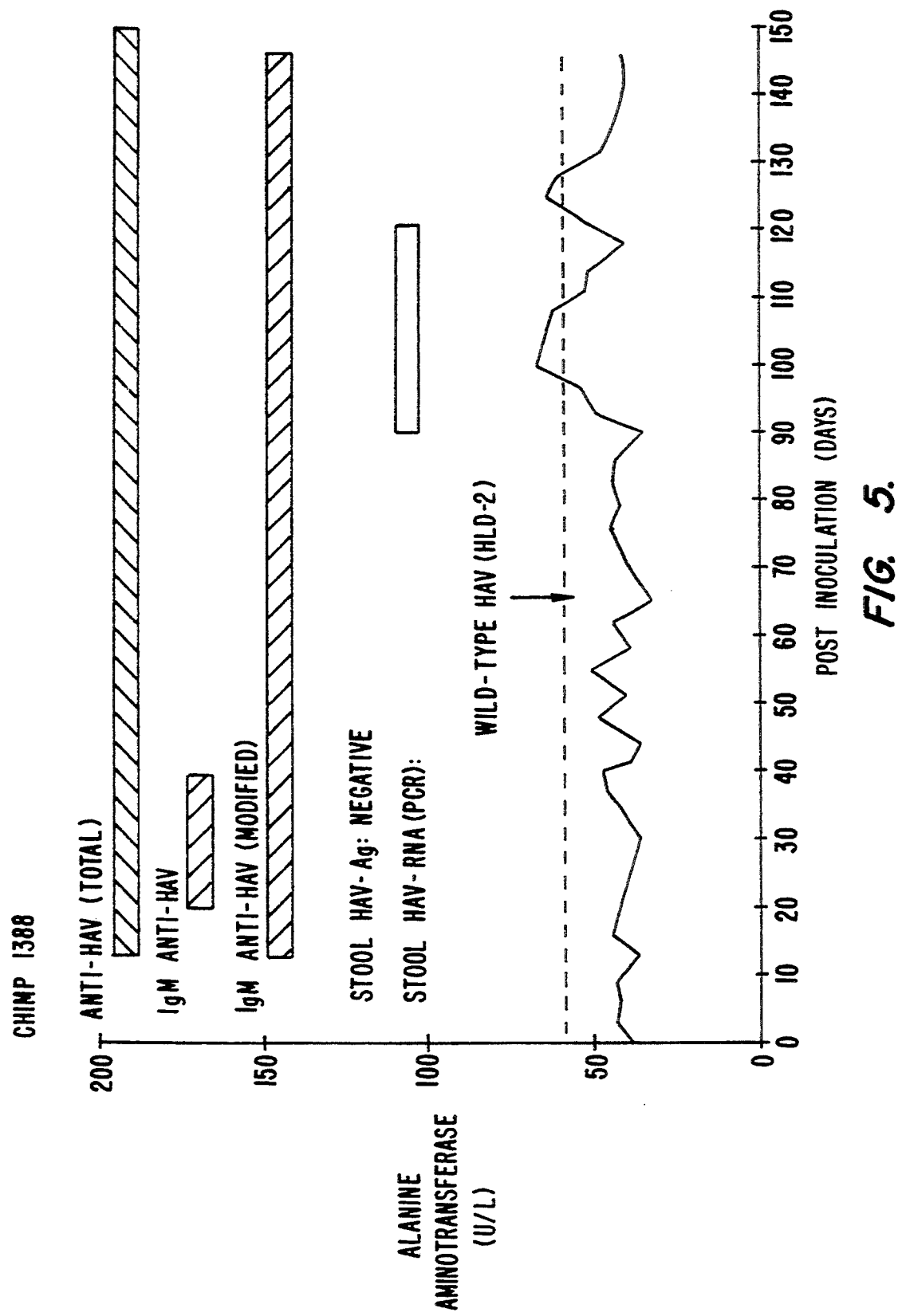
FIG. 5. Chimpanzee 1388 inoculated intravenously with liver suspension from cynomolgus macaque JM 55. ------ represents cutoff value (99% confidence) for ALT calculated from the values during the month prior to inoculation.
Figure 6:
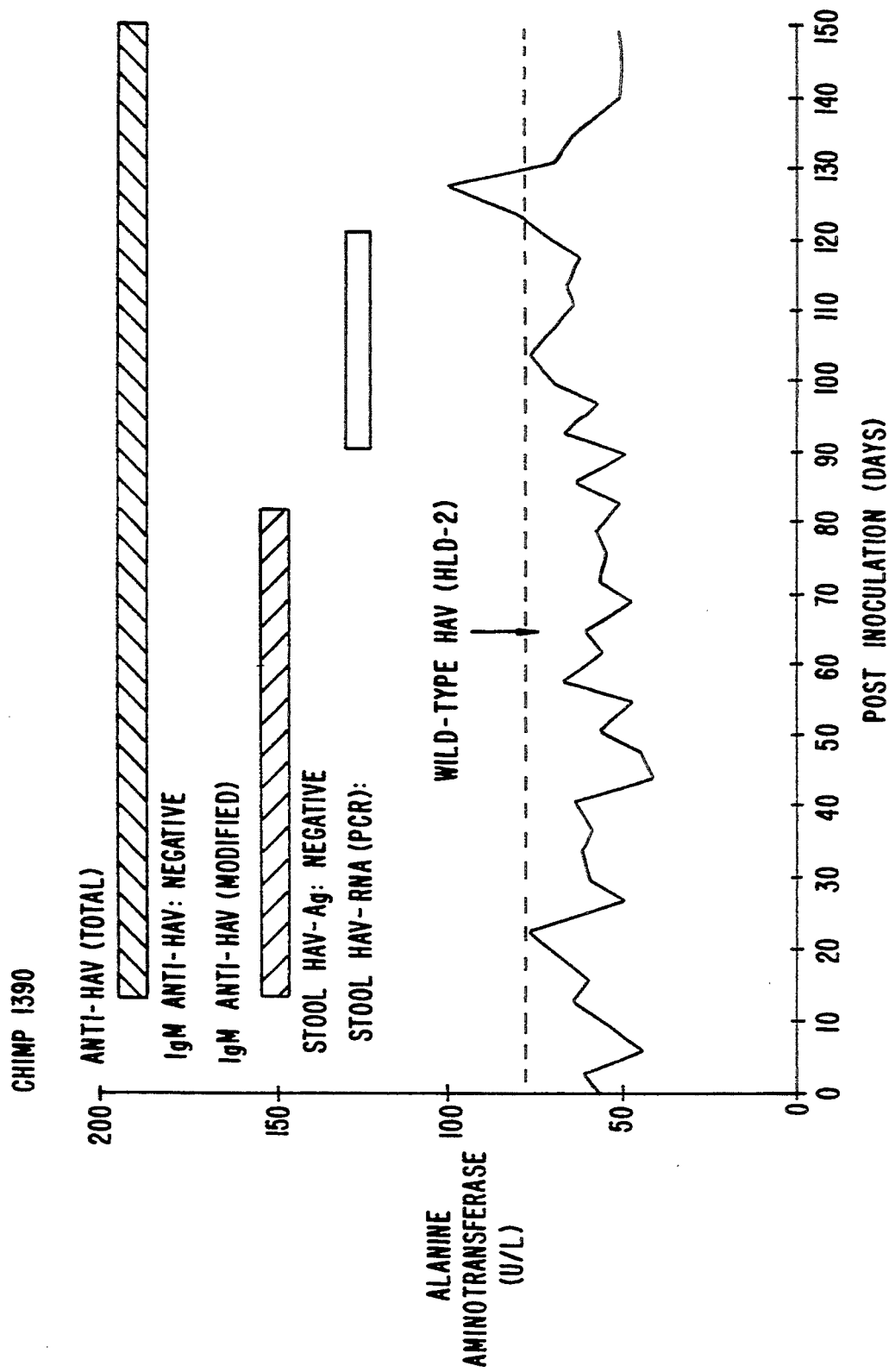
FIG. 6. Chimpanzee 1390 inoculated intravenously with liver suspension from cynomolgus macaque JM 55. ------ represents cutoff value (99% confidence) for ALT calculated from the values during the month prior to inoculation.

Chimpanzees were inoculated intravenously with 1.0 ml of 10% liver suspension from cynomolgus macque JM 55. On day 65 post inoculation, they were inoculated intravenously with 1.0 ml of a 10% stool suspension containing wild-type HAV previously shown to be infectious (HLD-2). When injected into a chimpanzee intravenously, the cynomolgus hepatitis A virus induces an antibody response (anti-HAV) that is detected by current immunoassays (FIGS. 5 and 6). The cynomolgus virus does not produce evidence of clinical infection such as elevated liver enzymes (ALT) and that the virus is not shed in the stool as determined by a very sensitive technique, amplification by the polymerase chain reaction (PCR).

When the chimpanzees were challenged with a well pedigreed human virus known to produce infection (with high ALT elevations) in chimpanzees, the antibody induced by the cynomolgus HAV provides partial protection from infection as shown by a minimal rise in liver enzymes and shedding of virus in stool that is only detectable by PCR amplification (FIGS. 5 and 6).

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A DNA molecule encoding the capsid proteins from a cynomolgus monkey hepatitis A virus said molecule defined by the presence of nucleic acid encoding VP0, VP1 and VP3 where the molecule further encodes: i. an alanine at the amino acid residue number 70 of VP3 and an alanine at the amino acid residue number 102 of VP1 where said residues correspond to positions 315 and 593 of Seq. ID. No. 1 and ii. encoding the amino acid pair glutamine and threonine at the VP3-VP1 cleavage site.

2. A nucleotide sequence of claim 1 wherein the sequence is Seq. I.D. No. 1.

3. A nucleotide sequence of claim 1 having at least 95% residue identity on the nucleotide level with Seq. I.D. No. 1.

* * * * *